United States Patent
Zhang et al.

(10) Patent No.: US 10,067,078 B1
(45) Date of Patent: Sep. 4, 2018

(54) TRANSMISSION ELECTRON MICROSCOPE SAMPLE ALIGNMENT SYSTEM AND METHOD

(71) Applicant: KING ABDULLAH UNIVERSITY OF SCIENCE AND TECHNOLOGY, Thuwal (SA)

(72) Inventors: Daliang Zhang, Thuwal (SA); Yu Han, Thuwal (SA); Kun Li, Thuwal (SA); Yihan Zhu, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 15/896,597

(22) Filed: Feb. 14, 2018

Related U.S. Application Data

(60) Provisional application No. 62/608,966, filed on Dec. 21, 2017, provisional application No. 62/490,967, filed on Apr. 27, 2017, provisional application No. 62/490,968, filed on Apr. 27, 2017.

(51) Int. Cl.
   *G01N 23/04* (2018.01)
   *H01J 37/28* (2006.01)
   *G01N 23/20058* (2018.01)
   *H01J 37/26* (2006.01)
   *H01J 37/244* (2006.01)

(52) U.S. Cl.
   CPC ....... *G01N 23/20058* (2013.01); *G01N 23/04* (2013.01); *H01J 37/244* (2013.01); *H01J 37/263* (2013.01); *H01J 37/28* (2013.01); *H01J 2237/2802* (2013.01); *H01J 2237/2823* (2013.01)

(58) Field of Classification Search
   CPC . G01N 23/20058; G01N 23/04; H01J 37/244; H01J 37/263; H01J 37/28; H01J 2237/2802; H01J 2237/2823
   USPC ................................. 250/306, 307, 310, 311
   See application file for complete search history.

(56) References Cited

U.S. PATENT DOCUMENTS

| | | |
|---|---|---|
| 2011/0174972 A1 | 7/2011 | Duden |
| 2014/0151553 A1* | 6/2014 | Ominami ................ H01J 37/18 250/307 |
| 2017/0309441 A1 | 10/2017 | Flanagan |

OTHER PUBLICATIONS

Azubel, M., et al., "Electron Microscopy of Gold Nanoparticles at Atomic Resolution," Science, Aug. 22, 2014, vol. 345, pp. 909-912.
Brivio, F., et al., "Relativistic Quasiparticle Self-Consistent Electronic Structure of Hybrid Halide Perovskite Photovoltaic Absorbers," Physical Review, Apr. 21, 2014, vol. B 89, pp. 155204-1-155204-6.

(Continued)

*Primary Examiner* — Nicole Ippolito
*Assistant Examiner* — Hanway Chang
(74) *Attorney, Agent, or Firm* — Patent Portfolio Builders PLLC

(57) ABSTRACT

A system and method involve applying an electron beam to a sample and obtaining an image of the sample with the applied electron beam. An orientation of the sample relative to the sample's zone axis is automatically determined based on a distribution of reflections in the image. The orientation of the sample is automatically adjusted to align with the sample's zone axis based on the determined orientation.

20 Claims, 9 Drawing Sheets

(56) References Cited

OTHER PUBLICATIONS

Cavka, J.H., et al., "A New Zirconium Inorganic Building Brick Forming Metal Organic Frameworks With Exceptional Stability," Journal of the American Chemical Society, Sep. 26, 2008, vol. 130, pp. 13850-13851.
Chui, S.S., et al., "A Chemically Functionalizable Nanoporous Material [Cu3(TMA)2(H2O)3]n," Science, Feb. 19, 1999, vol. 283, pp. 1148-1150.
Cravillon, J., et al., "Rapid Room-Temperature Synthesis and Characterization of Nanocrystals of a Prototypical Zeolitic Imidazolate Framework," Chemistry of Materials, Mar. 26, 2009, vol. 21, pp. 1410-1412.
Duden, T., et al., "KSpaceNavigator as a Tool for Computer-Assisted Sample Tilting in High-Resolution Imaging, Tomography and Defect Analysis," Ultramicroscopy, Aug. 24, 2011, vol. 111, pp. 1574-1580.
Egerton, R.F., "Mechanisms of Radiation Damage in Beam-Sensitive Specimens, for TEM Accelerating Voltages Between 10 and 300 kV," Microscopy Research and Technique, Jul. 17, 2012, No. 75, pp. 1550-1556.
Farha, O.K., et al., "De Novo Synthesis of a Metal-Organic Framework Material Featuring Ultrahigh Surface Area and Gas Storage Capacities," Nature Chemistry, Nov. 2010, vol. 2, pp. 944-948.
Furukawa, H., et al., "The Chemistry and Applications of Metal-Organic Frameworks," Science, Aug. 30, 2013, vol. 341, pp. 1230444-1-1230444-12.
Garcia, A., et al., "Analysis of Electron Beam Damage of Exfoliated MoS(2) Sheets and Quantitative HAADF-STEM Imaging," Ultramicroscopy, Jun. 2, 2014, vol. 146, pp. 33-38.
Guan, L.H., et al., "Smallest Carbon Nanotube Assigned With Atomic Resolution Accuracy," Nano Letters, Jan. 11, 2008, vol. 8, pp. 459-462.
Hashimoto, K., et al., "Direct Evidence for Atomic Defects in Graphene Layers," Nature, Aug. 19, 2004, vol. 430, pp. 870-873.
Jia, C.L., et al., "Atomic-Resolution Imaging of Oxygen in Perovskite Ceramics," Science, Feb. 7, 2003, vol. 299, pp. 870-873.
Jin, L., et al., "Applications of Direct Detection Device in Transmission Electron Microscopy," Journal of Structural Biology, Oct. 26, 2007, vol. 161, pp. 352-358.
Kilaas, R., "Optimal and Near-Optimal Filters in High-Resolution Electron Microscopy," Journal of Microscopy, Apr./May 1998, vol. 190, Parts 1/2, pp. 45-51.
Lebedev, O.I., et al., "First Direct Imaging of Giant Pores of the Metal-Organic Framework MIL-101," Chemistry of Materials, Dec. 1, 2005, vol. 17, pp. 6525-6527.
Li, H., et al. "Design and Synthesis of an Exceptionally Stable and Highly Porous Metal-Organic Framework," Nature, Nov. 18, 1999, vol. 402, pp. 276-279.
Li, X.M., et al., "Electron Counting and Beam-Induced Motion Correction Enable Near-Atomic-Resolution Single-Particle Cryo-EM," Nature Methods, Jun. 2013, vol. 10, pp. 584-590.
Liu, X., et al., "Isomorphous Incorporation of Tin Ions into Germanosilicate Framework Assisted by Local Structural Rearrangement," ACS Catalysis, Nov. 11, 2016, vol. 6, pp. 8420-8431.
Martin, J.D., et al., "Designing Intermediate-Range Order in Amorphous Materials." Nature, Sep. 2002, vol. 419, pp. 381-384.
Merk, A., et al., "Breaking Cryo-EM Resolution Barriers to Facilitate Drug Discovery," Cell, Jun. 16, 2016, vol. 165, pp. 1698-1707.
Meyer, J.C., et al., "Experimental Analysis of Charge Redistribution Due to Chemical Bonding by High-Resolution Transmission Electron Microscopy," Nature Materials, Mar. 2011, vol. 10, pp. 209-215.
Mitchell, D.R.G., HRTEM filter V1.3 (https://www.felmi-zfe.at/dm-script/dm-script-database/), downloaded from the internet Mar. 18, 2018.
Park, K.S., et al., "Exceptional Chemical and Thermal Stability of Zeolitic Imidazolate Frameworks," Proceedings of the National Academy of Sciences of the United States of America, Jul. 5, 2005, vol. 103, pp. 10186-10191.

QSTEM V2.31 (http://www.qstem.org), last modified Oct. 19, 2017, downloaded from the internet Mar. 18, 2018.
Roth, W.J., et al., "A Family of Zeolites With Controlled Pore Size Prepared Using a Top-Down Method," Nature chemistry, Jul. 2013, vol. 5, pp. 628-633.
Sichert, J.A., et al., "Quantum Size Effect in Organometal Halide Perovskite Nanoplatelets," Nano Letters, Sep. 1, 2015, vol. 15, pp. 6521-6527.
Sidorov, M.V., ctfExplorer V0.999a (http://www.maxsidorov.com/ctfexplorer), created May 21, 2000, last updated Apr. 19, 2017, downloaded from the internet Mar. 18, 2018.
Snaith, H.J., et al., "Anomalous Hysteresis in Perovskite Solar Cells," The Journal of Physical Chemistry Letters, Mar. 24, 2014, vol. 5, pp. 1511-1515.
Susi, T., et al., "Atomistic Description of Electron Beam Damage in Nitrogen-Doped Graphene and Single-Walled Carbon Nanotubes," ACS Nano, Sep. 24, 2012, vol. 6, No. 10, pp. 8837-8846.
Torad, N.L., et al., "Facile Synthesis of Nanoporous Carbons With Controlled Particle Sizes by Direct Carbonization of Monodispersed ZIF-8 Crystals," The Royal Society of Chemistry, Feb. 4, 2013, vol. 49, pp. 2521-2523.
Tress, W., et al., "Understanding the Rate-Dependent J-V Hysteresis, Slow Time Component, and Aging in CH3NH3PbI3 Perovskite Solar Cells: The Role of a Compensated Electric Field," Energy & Environmental Science, Jan. 5, 2015, vol. 8, pp. 995-1004.
Ugurlu, O., et al., "Radiolysis to Knock-on Damage Transition in Zeolites Under Electron Beam Irradiation," Physical Review, 2011, vol. B 83, pp. 113408-1-113408-4.
Valenzano, L., et al., "Disclosing the Complex Structure of UiO-66 Metal Organic Framework: A Synergic Combination of Experiment and Theory," Chemistry of Materials, Mar. 4, 2011, vol. 23, pp. 1700-1718.
Van De Walle, A., "A Complete Representation of Structure-Property Relationships in Crystals," Nature Materials, Jun. 2008, vol. 7, pp. 455-458.
Wan, W., et al., "Structure Projection Reconstruction From Through-Focus Series of High-Resolution Transmission Electron Microscopy Images," Ultramicroscopy, Jan. 31, 2012, vol. 115, pp. 50-60.
Wan, W., et al., "Three-Dimensional Rotation Electron Diffraction: Software RED for Automated Data Collection and Data Processing," Journal of Applied Crystallography, Oct. 9, 2013, vol. 46, pp. 1863-1873.
Wang, F.L., et al., "The Controlled Regulation of Morphology and Size of HKUST-1 by "Coordination Modulation Method"," Microporous and Mesoporous Materials, Feb. 26, 2013, vol. 173, pp. 181-188.
Wei, J., et al., "Hysteresis Analysis Based on the Ferroelectric Effect in Hybrid Perovskite Solar Cells," The Journal of Physical Chemistry Letters, Oct. 24, 2014, vol. 5, pp. 3937-3945.
Wei, Y.J., et al., "The Nature of Strength Enhancement and Weakening by Pentagon-Heptagon Defects in Graphene," Nature Materials, Sep. 2012, vol. 11, pp. 759-763.
Wiktor, C., et al., "Imaging of Intact MOF-5 Nanocrystals by Advanced TEM at Liquid Nitrogen Temperature," Microporous and Mesoporous Materials, Jun. 16, 2012, vol. 162, pp. 131-135.
Xu, Z.D., et al., "Pt@UiO-66 Heterostructures for Highly Selective Detection of Hydrogen Peroxide with an Extended Linear Range", Analytical Chemistry, Feb. 20, 2015, vol. 87, pp. 3438-3111.
Zaefferer, S., "New Developments of Computer-Aided Crystallographic Analysis in Transmission Electron Microscopy," Journal of Applied Crystallography, Feb. 2000, vol. 33, pp. 10-25 (Statement of Relevancy: There was a commercial program from TSL in the 90s called "TOCA" as part of a software package "ACT" where similar calculation/estimation of Laure circle was performed. A search for this program resulted in the attached paper.).
Zandbergen, Kw., et al., "The Use of Through Focus Exit Wave Reconstruction in the Structure Determination of Several Intermetallic Superconductors," Ultramicroscopy, Aug. 1996, vol. 64, pp. 231-247.
Zhu, L.K., et al., "Direct Observations of the MOF (UiO-66) Structure by Transmission Electron Microscopy," The Royal Society of Chemistry, Aug. 19, 2013, vol. 15, pp. 9356-9359.

(56) References Cited

OTHER PUBLICATIONS

Zhu, Y., "Unravelling Surface and Interfacial Structures of a Metal-Organic Framework by Transmission Electron Microscopy," Nature Materials, Feb. 20, 2017, vol. 16, pp. 532-536.
Zhu, Y.H., et al., "Atomic Resolution Imaging of Nanoscale Structural Ordering in a Complex Metal Oxide Catalyst," Chemistry of Materials, Jul. 28, 2012, vol. 24, pp. 3269-3278.
Zhu, Y.H., et al., "Chiral Gold Nanowires with Boerdijk-Coxeter-Bemal Structure," Journal of the American Chemical Society, Aug. 15, 2014, vol. 136, pp. 12746-12752.
Zhu, Y.H., et al., "Direct Observation of Surface Reconstruction and Termination on a Complex Metal Oxide Catalyst by Electron Microscopy," Angewandte Chemie International, Mar. 19, 2012, Edit 51, pp. 4176-4180.
Zou, X.D., et al., "Electron Crystallography: Electron Microscopy and Electron Diffraction," Oxford University Press, 2011, pp. 177-190.
Jansen, J., et al.; "Towards automatic alignment of a crystalline sample in an electron microscope along a zone axis"; Ultramicroscopy, vol. 125, XP055473754; Nov. 5, 2012; pp. 59-65.
Zhang, D., et al.; "Atomic-resolution transmission electron microscopy of electron beam-sensitive crystalline materials"; Science, vol. 359, No. 6376; XP055473443; Jan. 18, 2018; pp. 675-679.
Zhang, D., et al.; "Supplementary Materials for Atomic-resolution transmission electron microscopy of electron beam-sensitive crystalline materials"; Science; XP055474073; Jan. 18, 2018; pp. 1-26.
Invitation to Pay Additional Fees and, Where Applicable, Protest Fee in International Application No. PCT/IB2018/050910. (All references not cited herewith have been previously made of record.).

\* cited by examiner

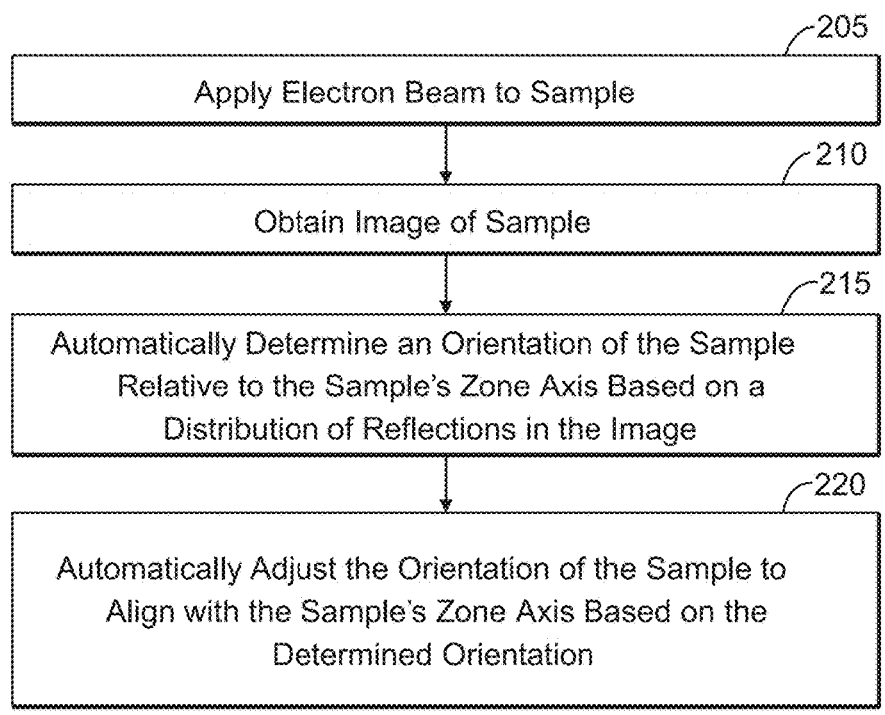

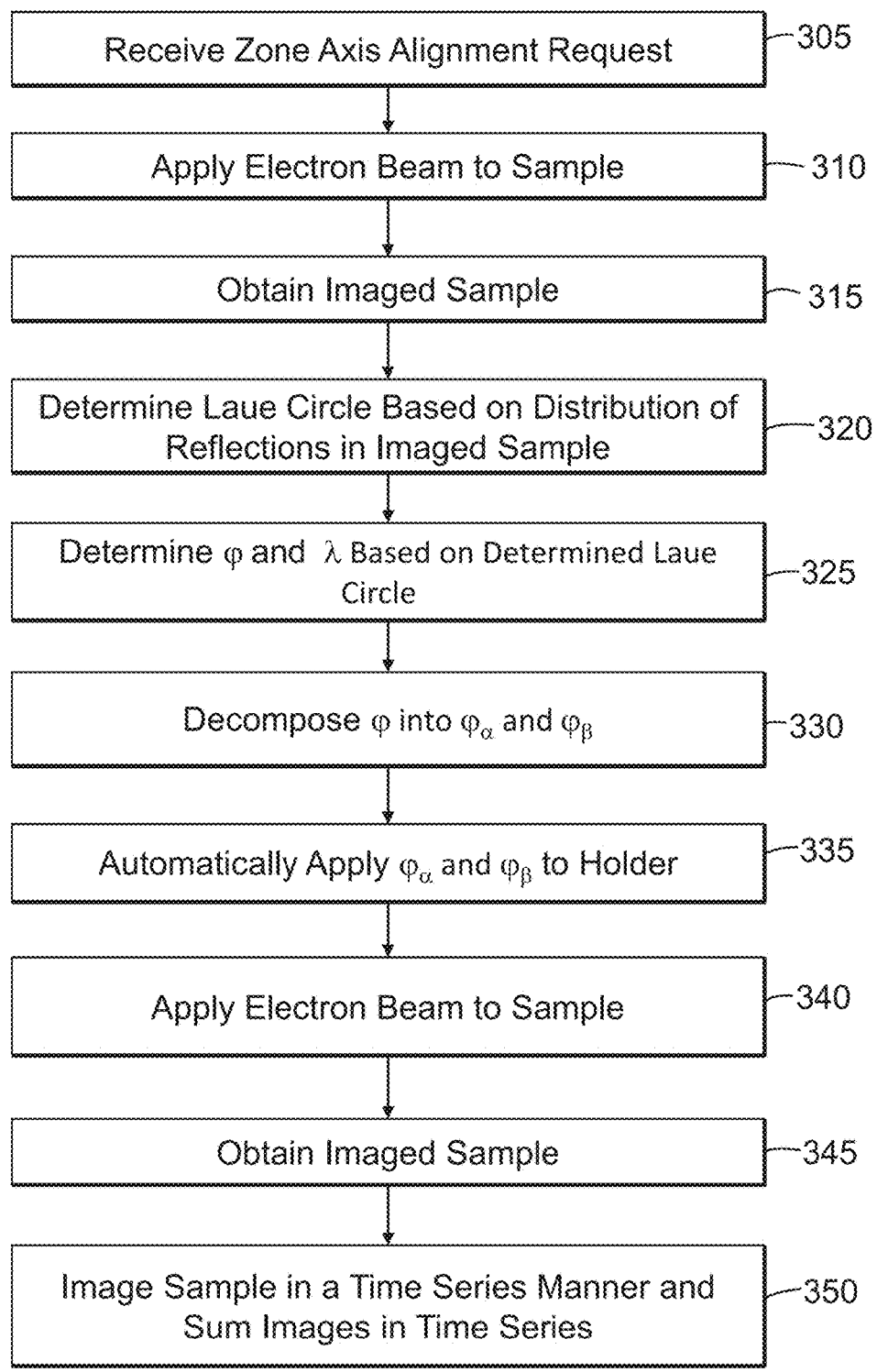

FIG. 4A 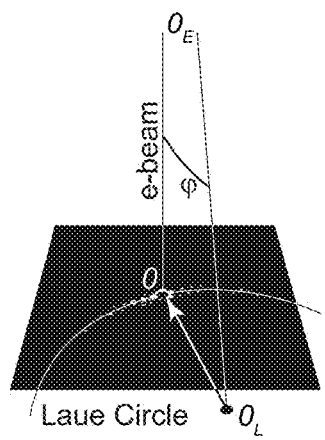 FIG. 4B 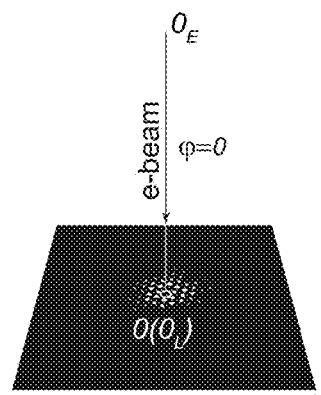 FIG. 4C 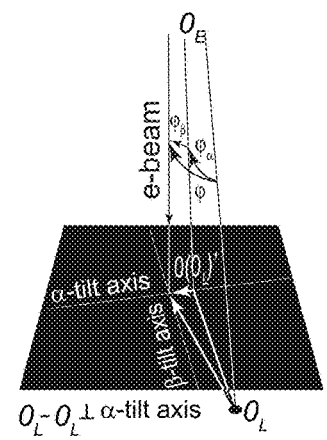
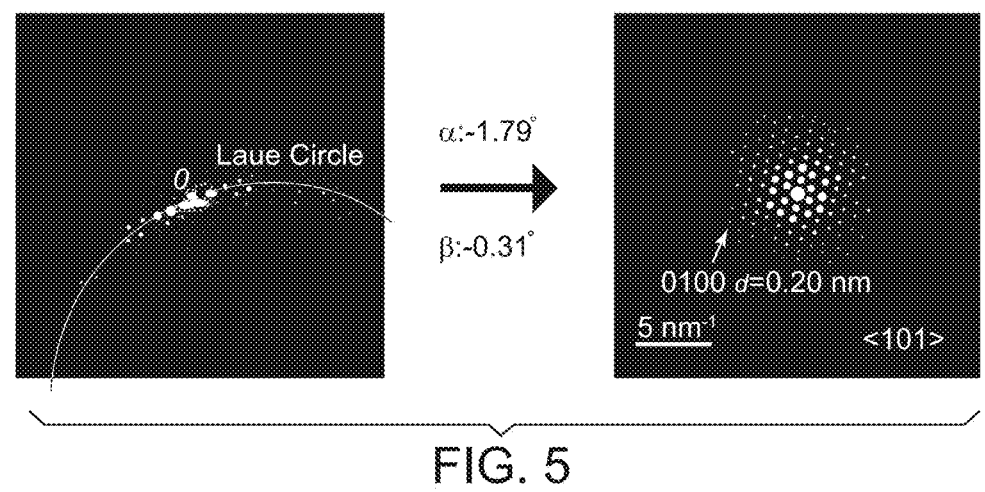
FIG. 5

TRANSMISSION ELECTRON MICROSCOPE SAMPLE ALIGNMENT SYSTEM AND METHOD

BACKGROUND

Technical Field

Embodiments of the subject matter disclosed herein generally relate to systems and methods for aligning a sample for a transmission electron microscope (TEM).

Discussion of the Background

TEMs are commonly used for high resolution transmission electron microscopy (HRTEM) to image crystalline solids consisting of periodically arranged atoms. To reveal the symmetry of the materials, an HRTEM image must be taken with the sample aligned along certain directions, commonly referred to as the zone axis. This alignment is typically a manual process requiring in-depth understanding of the crystallography of the sample, which is lacking for many operators of an TEM.

Operators with an in-depth understanding of the crystallography of the sample must also understand the tilting behavior of the sample holder. Such an operator performs theoretical calculations based on the understanding of the crystallography and the tilting behavior of the sample holder to determine the tilt corrections that need to be made to the sample holder. Further, the tilt correction inevitably results in some sample movement relative to the electron beam, which requires further correction by the operator.

This manual process not only requires specialized knowledge but also is time consuming, typically requiring tens of minutes to perform. Moreover, the operator must expose the sample to the electron beam a number of times, including an initial exposure to identify the current sample orientation and at least a second exposure to confirm the tilt correction did in fact align the sample along the zone axes. This manual process typically involves more than two exposures due to, for example, the sample movement and/or the initial correction not completely aligning with the zone axes. These additional exposures can damage samples of materials sensitive to the electron beam (e.g., some materials can be damaged by a cumulative electron doses of less than 10 electrons per $Å^2$ and many materials can be damaged by cumulative doses in the range of 10-20 $e^-Å^{-2}$), and thus result in a subsequent exposure for studying the sample being performed on a damaged sample. The types of damage include knock-on damage, heating damage, and radiolysis. Although knock-on damage can be addressed using low accelerating voltages (e.g., 60-120 kV), the use of low-energy electrons results in poor image resolution and short penetration depth.

One attempt to address the manual process for zone access alignment involved a computer-assisted tool that evaluated intensity asymmetries in a diffraction pattern to determine the offset of the sample relative to its zone axis. Relying upon the intensity of reflections, however, can result in inaccurate alignment due to the influence of structure factors (i.e., the mathematic concept used to calculate kinematical diffraction intensity form the content of a unit cell) or dynamical effects (i.e., when a crystal is big enough, diffraction phenomenon can happen more than one time and the intensity of diffraction can be different than the values calculated from the structure factor).

Thus, there is a need for methods and system that does not require an operator to have an in-depth understanding of the crystallography and tilting behavior of the sample holder and that minimizes the number of exposures of the sample to the electron beam to align the zone axes and is not influenced by structure factors and other dynamic effects.

SUMMARY

According to an embodiment, there is a method involving applying an electron beam to a sample and obtaining an image of the sample with the applied electron beam. An orientation of the sample relative to the sample's zone axis is automatically determined based on a distribution of reflections in the image. The orientation of the sample is automatically adjusted to align with the sample's zone axis based on the determined orientation.

According to another embodiment, there is a system, which includes an electron gun, a sample holder, an imaging detector, and a positioning controller coupled to the sample holder and configured to adjust an orientation of a sample in the sample holder. The system also includes a processor communicatively coupled to the electron gun, the sample holder, the imaging detector, and the positioning controller. The processor executes instructions to control the sample holder based on an automatically calculated Laue circle of the imaged sample.

According to a further embodiment, there is a method involving automatically determining an orientation of a sample relative to the sample's zone axis based on a distribution of reflections in an image of the sample. The orientation of the sample is automatically adjusted to align with the sample's zone axis based on the determined orientation. An amplitude filtered pattern is calculated in a Fourier domain based on amplitude components of a plurality of Fourier transformed images of a sequence of images. An amplitude component of the plurality of Fourier transformed images is replaced with the amplitude pattern to form a plurality of filtered Fourier transformed images. Image shift information is determined based on the plurality of filtered Fourier transformed images. The image shift information is applied to images in the sequence of images to form a plurality of aligned images.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 2 illustrates a flowchart of a method for automatic zone axis alignment of a sample according to an embodiment;

FIGS. 3A-3C illustrate flowcharts of methods for automatic zone axis alignment of a sample according to embodiments;

FIG. 4A illustrates a Laue Circle of a sample according to an embodiment;

FIG. 4B illustrates a sample after automatic zone axis alignment according to an embodiment;

FIG. 4C illustrates an intersection of a Laue Circle and an Ewald sphere according to an embodiment;

FIG. 5 illustrates a sample before and after automatic zone axis alignment according to an embodiment;

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of high resolution transmission electron microscopy (HRTEM). However, the embodiments to be discussed next are not limited to HRTEM but may be applied to any type of microscopy in which the imaging beam can damage a sample during zone axis alignment.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment an electron beam is applied to a sample and an image of the sample with the applied electron beam is obtained. An orientation of the sample relative to the sample's zone axis is automatically determined based on a distribution of reflections in the image. The orientation of the sample is automatically adjusted to align with the sample's zone axis based on the determined orientation. Those skilled in the art would understand the zone axis refers to orientations of a crystal showing high-symmetry and generally refers to any direction referenced to the direct lattice of a crystal in three dimensions.

Figure 1:
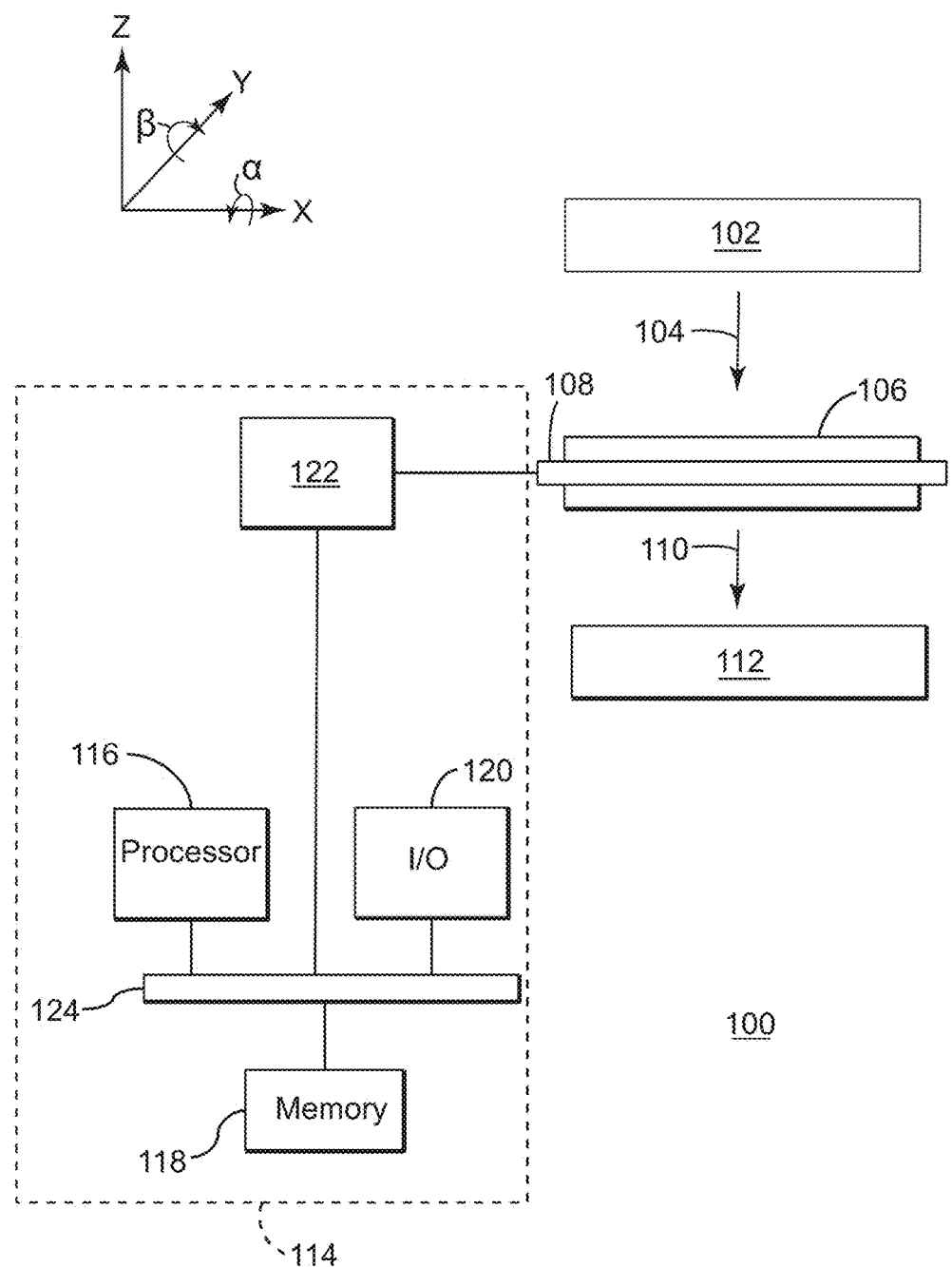
FIG. 1 is a schematic diagram of an apparatus for automatic zone axis alignment of a sample according to an embodiment.

FIG. 1 is a schematic diagram of an apparatus for automatic zone axis alignment of a sample according to an embodiment. The apparatus 100 is embodied as a transmission electron microscope (TEM). Specifically, an electron gun 102 applies an electron beam 104 to a sample 106, which is situated in a sample holder 108. A beam of electrons 110 passing through the sample 106 is received by an imaging detector 112, which can be film or a digital pixel detector, such as a direct-detection electron-counting (DDEC) camera (e.g., a Gatan K2 Summit) or a charge coupled device (CCD) camera. DDEC cameras are particularly useful due to the high detective quantum efficiency (DQE) that allows ultra-low electron doses. For example, a DDEC camera allows image acquisition at magnifications of at least 55,000 to achieve atomic resolution (i.e., a pixel size of 0.57 Å×0.57 Å) with an electron beam dose as lows as 2-4 $e^-$ per pixel (i.e., doses as low as 6-12 $e^-\text{Å}^{-2}$). Those skilled in the art will recognize an imaging detector represents a class of structures for obtaining an image of the sample 106.

The apparatus 100 also has a control system 114, which includes a processor 116, memory 118, input/output interface 120, and sample holder positioning controller 122, which can communicate with one another via bus 124. The input/output interface 120 allows an operator to communicate with the processor 116, memory 118, and/or the positioning controller 122 to operate the TEM. For example, the input/output interface 120 can include one or more displays for displaying samples imaged by imaging detector 112, as well as one or more input devices for manually controlling various aspects of the TEM (e.g., focus, sample positioning, etc.), and for initiating an automatic control of the TEM, as will be described in more detail below.

Those skilled in the art will recognize that the positioning controller 122 refers to a class of structures used by a TEM for controlling the orientation of sample. Although not illustrated for purposes of clarity, processor 116 is also communicatively coupled to electron gun 102 and imaging detector 112 via bus 124 to provide instructions to control these devices and receive outputs from these devices.

For ease of explanation some of the components of a TEM are not illustrated, however these additional components are not necessary for understanding the disclosed embodiments but nonetheless can be used with the disclosed embodiments.

As discussed above, conventional HRTEM studies require an operator with in-depth understanding of the crystallography of the sample and knowledge of the titling behavior of the sample holder. Such an operator would expose a sample to the electron beam, perform calculations and then use an input/output device to adjust the tilting of the sample by way of the sample holder. As illustrated in the upper-left hand corner of FIG. 1, the operator adjusts the orientation of the sample about the X-axis and Y-axis. In contrast, embodiments discussed in more detail below automatically adjust the sample orientation, which provides a more accurate alignment of the sample about the zone axis that minimizes the number and intensity of exposures of the sample for the orientation process. This automatic adjustment can be performed using processor instructions stored in memory 118 and executed by processor 116 using positioning controller 122 to control the orientation of the holder 108, and in turn the sample 106. Thus, these processor instructions can be loaded into a TEM to perform the methods discussed below.

FIG. 2 illustrates a flowchart of a method for automatic zone axis alignment of a sample according to an embodiment. Initially, the processor 116 instructs electron gun 102 to apply an electron beam 104 to sample 106 (step 205). The processor 116 then obtains an image of the sample 106 from imaging detector 112 (step 210) and, using processor instructions detailed below, automatically determines an orientation of the sample 106 relative to its zone axis based on a distribution of reflections in the image (step 215). The processor 116, based on the determined orientation, automatically instructs positioning controller 122 to adjust the orientation of the sample 106 to align its zone axis (step 220). The processor 116 can adjust the orientation of sample 106 by sending an amount of adjustment about the X-axis and/or Y-axis or can send commands to start and stop the adjustment in either or both axes.

The obtained image of the sample can be quite noisy, which can result in small errors in the automatic determination of the sample orientation, as well as the automatic adjustment of the sample orientation. Thus, if the sample is not completely aligned along its zone axis after the sample orientation is automatically adjusted, steps 205-220 can be repeated to reduce the error. Recognition of whether the sample is orientated along its zone axis can be determined by an operator viewing the sample (in-depth understanding the crystallography of the sample is not required to identify the sample not being aligned along its zone axis) or can be performed automatically by processor 116.

The automatic zone axis alignment can be performed using a dose of, for example, ~0.15 e/Å$^2$, whereas conventional manual processes involve electron doses of more than tens of electrons per Å$^2$. This electron dosage difference can be significant for an HTREM study of, for example, radiation sensitive crystals with structures that change after total electron doses of 15 e/Å$^2$ to ~20 e/Å$^2$. The disclosed automatic zone axis alignment therefore provides the ability to perform more studies and/or at higher electron doses compared to a manual zone axis alignment.

Figure 3B:
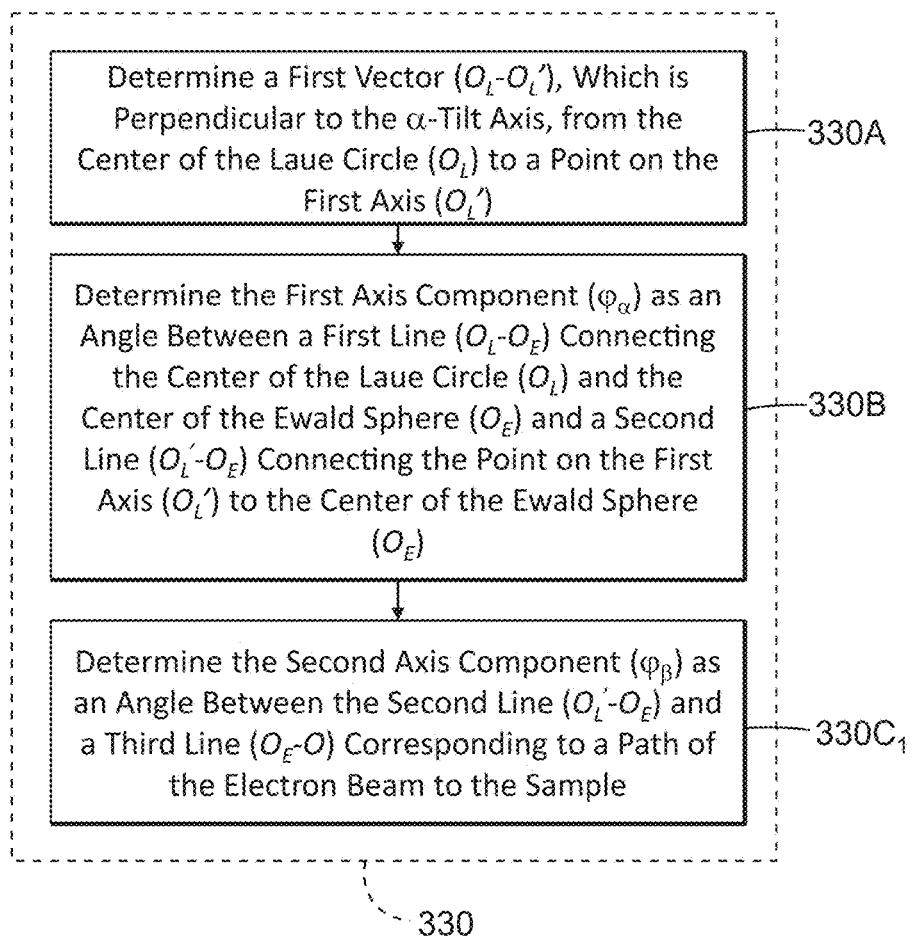
Figure 3C:
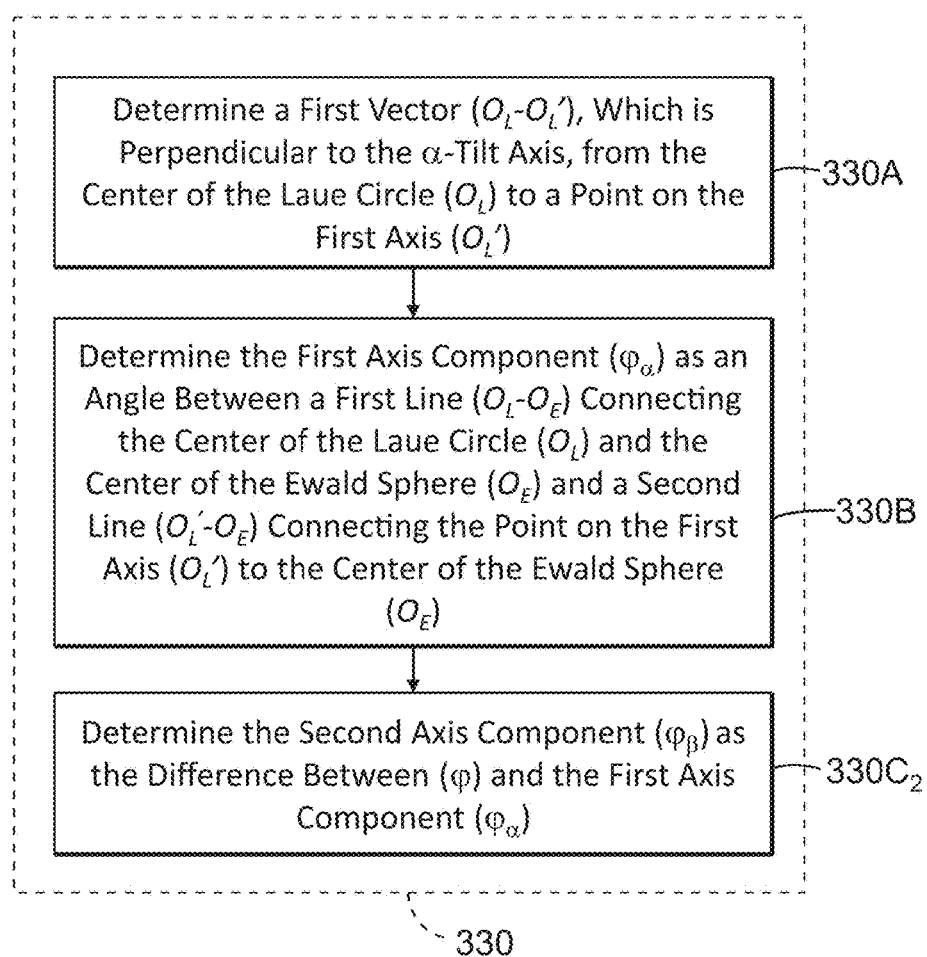

FIGS. 3A-3C illustrate flowcharts of methods for automatic zone axis alignment of a sample according to embodiments. Initially, the processor 116 receives a zone axis alignment request from an operator, for example via input/output device 120 (step 305). The processor 116 instructs the electron gun 102 to apply an electron beam 104 on sample 106 (step 310). The electron beam density can be, in a non-limiting example, 0.03 e/Å$^2$/s with an exposure time of 2 seconds.

The processor 116 then obtains the imaged sample from imaging detector 112 (step 315). The sample can be imaged in the diffraction mode, which can also be referred to as the reflection mode. The processor 116 then determines the sample's Laue circle based on the distribution of reflections in the imaged sample forming a portion of the circumference of the Laue circle (step 320). A non-limiting example of this is illustrated in FIG. 4A, in which O corresponds to the origin of the reciprocal lattice, $O_E$ corresponds to the center of the Ewald sphere, $O_L$ corresponds to the center of the Laue circle, $\varphi$ corresponds to an angle of the sample's deviation from zone axis alignment, direction $O_E \rightarrow O$ corresponds to the electron beam incidence, and direction $O_E \rightarrow O_L$ corresponds to the zone axis.

The observed electron diffraction pattern of the imaged sample can be understood as the interaction between the reciprocal lattice of the crystal and Ewald sphere and when the incidence of the electron beam (e-beam in the Figure) deviates from the sample's zone axis by an angle $\varphi$, the zero-order Laue zone (ZOLZ) of the lattice intersects the Ewald sphere, thus forming the Laue circle. The radius of the Ewald sphere $O_E$-O is $1/\lambda$, where $\lambda$ is the wavelength of the electron beam. Because the Laue circle passes through the reciprocal lattice O, the Laue circle's radius O-$O_L$ is approximately equal to $\sin(\varphi) \cdot (1/\lambda)$. Therefore, reducing the angle $\varphi$ decreases the radius of the Laue circle and when the angle $\varphi$ is 0 the electron beam incidence along the zone axis corresponds to the ZOLZ tangent to the Ewald sphere, an example of which is illustrated in FIG. 4B. Moving the $O_L$ until it coincides with O is the equivalent of changing the alignment of the sample from "off-axis" to "on-axis."

Accordingly, returning to FIG. 3A, the processor 116 uses the determined Laue circle to determine $\varphi$ and $\lambda$ consistent with the discussion above (step 325). The processor 116 then decomposes $\varphi$ into its constituent components $\varphi_\alpha$ and $\varphi_\beta$, where $\alpha$ and $\beta$ are axes that are respectively parallel to the x- and y-axes and the $\alpha$-tilt axis is parallel with the long dimension of the sample holder 108 (step 330). The calculation of components $\varphi_\alpha$ and $\varphi_\beta$ assumes both the $\alpha$-tilt and $\beta$-tilt axes are parallel to the plane of the electron diffraction. Although the $\beta$-tilt axis moves out of the plane once the $\alpha$ tilting is applied, the method provides an approximation with satisfactory results when the initial crystal orientation is relatively close to the zone axis, for example $-5° < \varphi < 5°$. Orientations outside of this range provide electron diffractions having very few observable reflections, which can make the determination of the Laue circle difficult.

Referring now to FIGS. 3B and 4C, processor 116 determines a first vector $O_L$-$O_L'$, which is perpendicular to the $\alpha$-tilt axis, from the center of the Laue circle $O_L$ to a point on the first axis $O_L'$, which in this example is the $\alpha$-tilt axis (step 330A). The processor 116 then determines the first axis component $\varphi_\alpha$ as an angle between a first line $O_L$-$O_E$ connecting the center of the Laue circle $O_L$ and the center of the Ewald sphere $O_E$ and a second line $O_L'$-$O_E$ connecting the point on the first axis $O_L'$ to the center of the Ewald sphere $O_E$ (step 330B). The processor 116 determines the second axis component $\varphi_\beta$ as an angle between the second line $O_L'$-$O_E$ and a third line $O_E$-O corresponding to the path of the electron beam to the sample (step 330C$_1$). Alternatively, as illustrated in FIG. 3C, the second axis component $\varphi_\beta$ can be determined as a difference between the determined angle $\varphi$ and the angle of the first axis component $\varphi_\alpha$ (step 330C$_2$).

Returning to FIG. 3A, the processor 116 then automatically applies $\varphi_\alpha$ and $\varphi_\beta$ to sample holder 108, which can be performed using positioning controller 122 in the manner discussed above (step 335). This positioning also ensures the sample is within the aperture of the electron beam 104. The processor 116 instructs the electron gun 102 to apply another electron beam dose on the sample 106 (step 340) and obtains another image of the sample (step 345). The HTREM study is then conducted by imaging the sample in a time series manner to produce a plurality of images that are subsequently summed in a time series manner into a final image for study (step 350).

The second imaging of the sample is used to confirm the sample's zone axis alignment, which with the automatic process of the disclosed embodiments should result in alignment. In contrast, for conventional manual alignment techniques this second imaging typically reveals that additional adjustments are required for zone axis alignment requiring additional applications of the electron beam to the sample, which for radiation sensitive crystals may result in damage to the crystals and/or reduce the amount of radiation employed for the HTREM study itself. Even if more than two imagings are required using this method, the overall electron dose can be limited to less than 2 e/Å$^2$. If a second imaging is required, steps 310-335 are repeated until the sample is aligned with its zone axis.

FIG. 5 illustrates a sample before and after automatic zone axis alignment according to an embodiment. In this example, initial electron beam dosage was 0.03 e/Å$^2$/s with an exposure of 2 seconds, which resulted in the image on the left-hand side of the figure. Using this image, the tilting angles were determined to be $\varphi_\alpha$: $-1.79°$ and $\varphi_\beta$: $-0.31°$, which when applied to the sample holder resulted in the image on the right-hand side of the figure in a second imaging. In this example, the overall electron dose to produce the two images was ~0.15 e/Å$^2$, which as illustrated in the right-hand side image provided successful zone axis alignment and thus reveals the symmetry of the sample.

The methods described above assume that the exact directions of the $\alpha$- and $\beta$-axes of the sample holder for a particular transmission electron microscope are known. If not, a pre-calibration of the directions of the $\alpha$-tilt and $\beta$-tilt axes and tilting accuracy of the sample holder should be performed for the transmission electron microscope, for example using a standard single-crystalline sample. This pre-calibration can be performed once for a particular transmission electron microscope and then the methods can be performed for one or more samples with the calculated tilting directions accounting for the pre-calibration. In other words, after the pre-calibration, the zone axis alignment can be automatically performed for any number of samples.

It will be recognized that during the HRTEM study, the sample, being a beam-sensitive material, can move due to beam-induced sample motion, which results in blurred images. Thus, the images from the HRTEM study should be aligned with each other. One way to align the images involves converting the images into the Fourier domain and then using the phase variation in the Fourier transformed images. However, HRTEM studies typically involve noisy images, which affects the accuracy of phase determination. The impact of noise can be minimized by selectively analyzing pixels in the Fourier transformed images with strong amplitudes, because phase determination of weak pixels is more easily influenced by noise and prone to errors. This can be achieved using an amplitude filter to confine the phase analysis to reliable strong-amplitude pixels.

Unlike the common methods that deal with the weak signals of individual images, the amplitude filter starts by combining the amplitude components of all of the Fourier transformed images in a time series of images to form an amplitude pattern. The amplitude pattern pinpoints the strong-amplitude pixels, as the reflections have invariable coordinates in the Fourier transformed images, irrespective of image drift. This results in hidden reflections emerging in the amplitude pattern. Background and weak pixels having amplitudes lower than a set threshold are filtered out from the amplitude pattern to form an amplitude filtered pattern. The amplitude filtered pattern is combined with the phase components from the original Fourier Transformed images to generate a series of modified Fourier Transformed images. This is followed an inverse Fourier Transformed being applied to the modified Fourier Transformed images to generate a series of filtered images.

Finally, the image drift can be calculated using iterative cross-correlation based on the filtered images, and this information can be used to align the original images in the time series of images. The drift-corrected, summed image shows rich high-resolution structural details, whereas cross-correlation without the amplitude filter cannot correctly align the image time series of images until it is 1×1×10 binned, which results in a marked reduction in image resolution in the direction of the image drift.

Figure 6:
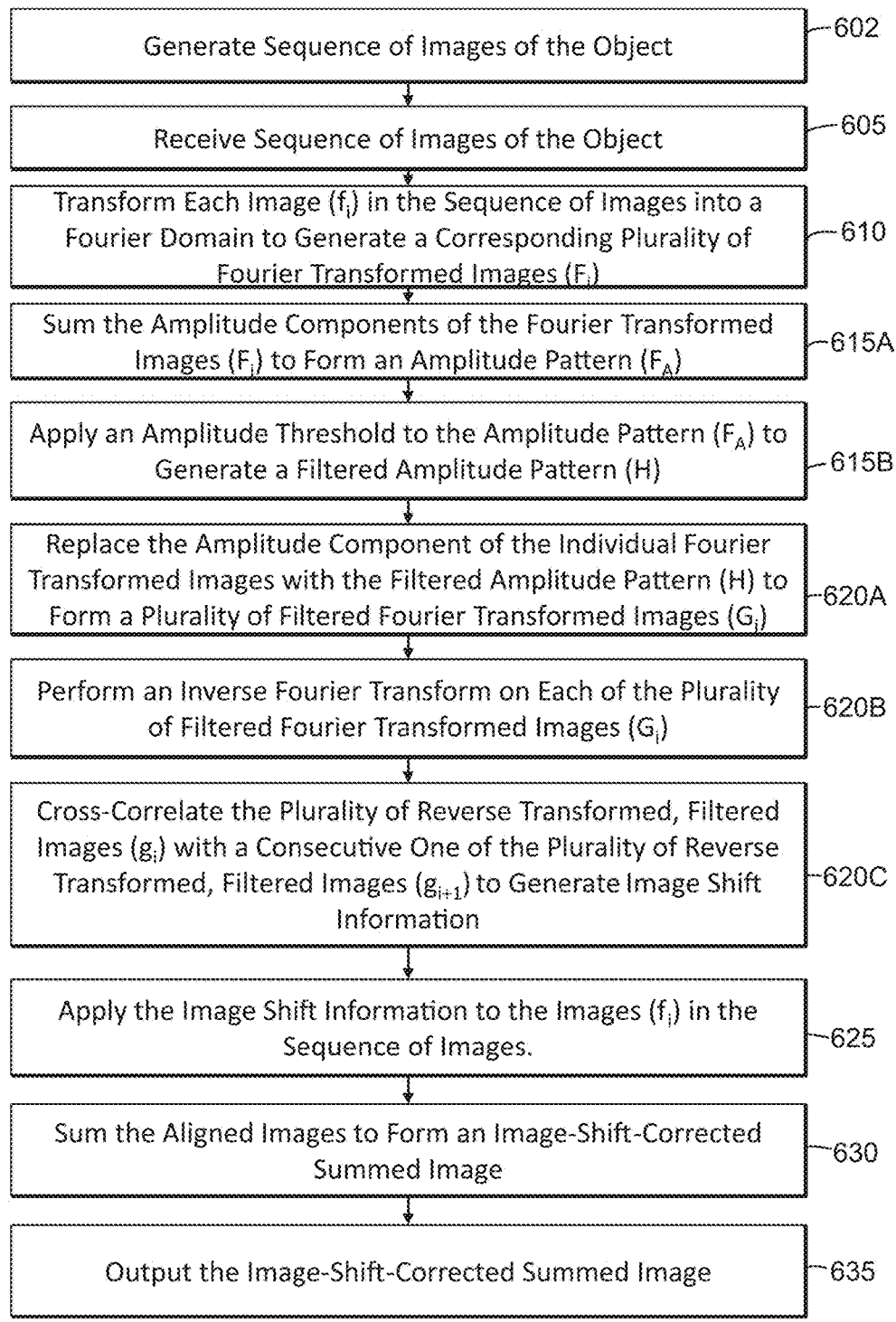
FIG. 6 illustrates a flowchart of a method for aligning a time series of images according to an embodiment.
Figure 7A:
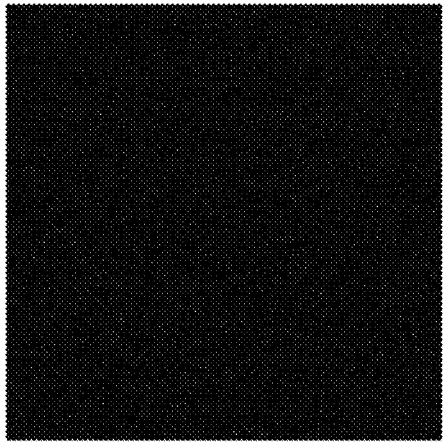
FIGS. 7A-7D, 7F, and 7G are images of an object used for aligning a time series of images according to an embodiment.

FIG. 6 illustrates a flowchart of a method for aligning a time series of images according to an embodiment. Initially, the processor 116 controls the electron gun 102 and imaging detector 112 to generate a sequence of images of the object by applying an electron beam to the object for a plurality of distinct time periods (step 602). FIG. 7A is an example of one individual image from the sequence of images, which shows the individual image is very noisy and the contrast is close to noise level, which can be due to the very short exposure time for capturing the individual image and/or the low electron dose applied to generate the image. The plurality of distinct time periods corresponds to a number of images in the sequence of images.

The image in FIG. 7A and all other example images illustrated in the figures were captured using a Titan Image Cs corrected Cube Transmission Electron Microscope (FEI) equipped with a K2-IS CMOS camera (manufactured by Gatan, Inc.), with 0.05 s exposure per image, 120 images in total, and a mean count of approximately 0.013 e/pixel in each individual image. The object imaged is a UiO-66 nano-sized Metal Organic Framework (MOF) crystal. In contrast, conventional techniques require a dose greater than 0.67e$^-$ per pixel per frame to attain sufficient a signal-to-noise ratio for reliable alignment.

The processor 116 receives a sequence of images ($f_1(x,y)$), ($f_2(x,y), \ldots,$ ($f_n(x,y)$)) of an object from imaging detector 112 (step 605), which as discussed above includes at least two consecutive images of the sequence of images spatially shifted relative to each other. The processor 116 then transforms each image ($f_i$) in the sequence of images ($f_1(x,y)$, $f_2(x,y), \ldots,$ ($f_n(x,y)$)) into a Fourier domain using a Fourier transform to generate a corresponding plurality of Fourier transformed images ($F_i$) (step 610). For a sequence of images containing i images ($f_1(x,y), f_2(x,y), \ldots, f_n(x,y)$), the Fourier transform of one individual image ($f_i(x,y)$) is:

$$F_i(u,v) = \iint f_i(x,y) e^{-2\pi i(ux+vy)} dx dy \quad (1)$$

The equation in polar form is as follows:

$$F_i(u,v) = |F_i(u,v)| e^{-\phi(u,v)} \quad (2)$$

where $|F_i(u,v)|$ is the amplitude and $\phi(u,v)$ is the phase of $F_i(u,v)$.

The processor 116 calculates an amplitude filtered pattern in the Fourier domain by summing the amplitude components of the Fourier transformed images ($F_i$) to form an amplitude pattern ($F_A$) (step 615A) and then applying an amplitude threshold to the amplitude pattern ($F_A$) to generate an amplitude filtered pattern (H) (step 615B). The amplitude filtered pattern (H) includes pixels in the amplitude pattern ($F_A$) having an amplitude at or above the amplitude threshold. Specifically, the Fourier transform amplitude components from all of the images in the sequence of images forms the amplitude pattern ($F_A$), which can be denoted as:

$$F_A(u,v) = \Sigma_{n=1}^{i} |F_i(u,v)| \quad (3)$$

In one non-limiting embodiment, the amplitude threshold $I_t$ can be a value in the following range:

$$I_t > 2 \times I_{mean} - I_{min} \quad (4)$$

Where $I_{mean}$ and $I_{min}$ are the mean value and the minimum value among all of the pixels in the amplitude pattern ($F_A$). Equation (4) describes one example of how to calculate the amplitude threshold $I_t$ and it should be recognized that there are many other ways to calculate the amplitude threshold $I_t$.

An amplitude filtered pattern can be represented by:

$$H(u,v) = \begin{cases} I_{uv} - I_t & \text{if } I_{uv} \geq I_t \\ 0 & \text{if } I_{uv} < I_t \end{cases} \quad (5)$$

where $I_{uv}$ is the intensity value at point (u,v) in the amplitude pattern $F_A(u,v)$. Equation (5) describes on example of how to calculate the amplitude filtered pattern H(u,v) and it should be recognized that there are many other ways to calculate the amplitude filtered pattern H(u,v). One of these alternatives could involve keeping the value $I_{uv}$ if $I_{uv} I_t$ (instead of using the value $I_{uv} - I_t$).

Figure 7B:
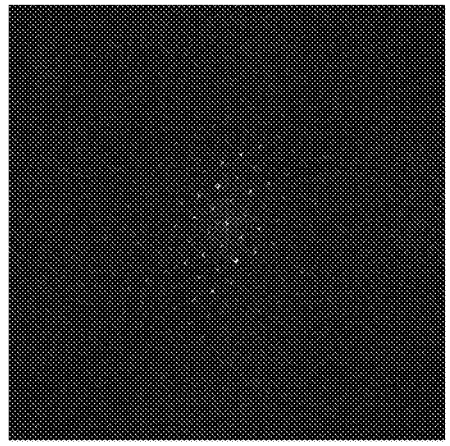
Figure 7C:
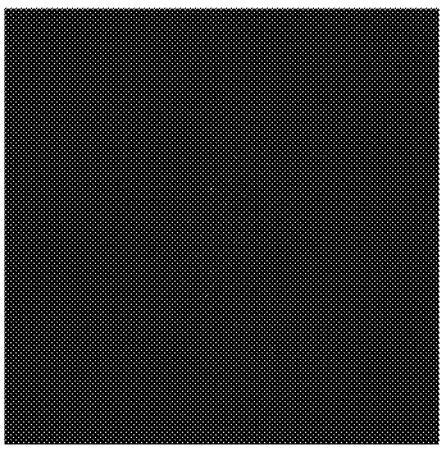

As illustrated in FIG. 7B, the amplitude pattern ($F_A$) reduces the signal-to-noise ratio so that the amplitude peaks corresponding to the atomic structure of the imaged object can be observed above the noise. The image in FIG. 7C is the amplitude filtered pattern H(u,v), which eliminates all pixels in the amplitude pattern having an amplitude value below the amplitude threshold of the amplitude filter while retaining the pixels having an amplitude value above the amplitude threshold of the amplitude filter. The image in FIG. 7C was produced using an amplitude threshold that eliminates all pixels except those corresponding to approximately 100 pixels having the highest amplitude in the Fourier transformed and summed image. Thus, for example, the amplitude threshold can be set to result in a predetermined number of pixels in the amplitude filtered pattern (H).

Next, the processor 116 replaces the amplitude component $|F_i(u,v)|$ of the individual Fourier transformed images $F_i(u,v)$ with the amplitude filtered pattern $H(u,v)$ to form a plurality of filtered Fourier transformed images ($G_i$) (step 620A), which can be represented by the following equation:

$$G_i(u,v) = H(u,v)e^{-i\phi(u,v)} \qquad (6)$$

The processor 116 then performs an inverse Fourier Transform on each of the plurality of filtered Fourier transformed images ($G_i$) to generate a corresponding plurality of reverse transformed, filtered images ($g_i$), (step 620B). Specifically, each filtered image $g_i(x,y)$ is represented by:

$$g_i(x,y) = \iint G_i(u,v)e^{2\pi i(ux+vy)}\,du\,dv \qquad (7)$$

Figure 7D:
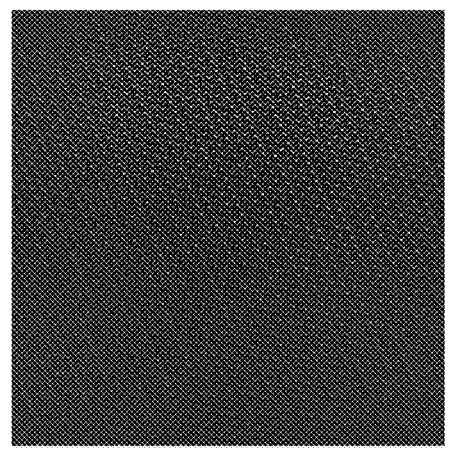

FIG. 7D illustrates an example of the image in FIG. 7A after having the amplitude component replaced by the amplitude filtered pattern (H) and then transformed back into the original domain. As can be observed, the lattice features of the imaged object become visible, whereas those features are not visible in the original, individual image illustrated in FIG. 7A.

The processor 116 then cross-correlates the plurality of reverse transformed, filtered images ($g_i$) with a consecutive one of the plurality of reverse transformed, filtered images ($g_{i+1}$) to generate image shift information for each of the plurality of reverse transformed, filtered images ($g_i$). (step 620C). Thus, no image shift information is calculated for the first image ($g_1$) and image shift information for each subsequent image ($g_{i+1}$) is based on the previous image in the sequence (i.e., $g_1$ for the second image and $g_{i-1}$ for each image after the second image). A fixed image is not used for the cross-correlation because the filtered image $g_i(x,y)$ contains a periodic lattice, and thus the determination of drifts only works for motions within a periodic unit. The use of consecutive images for cross-correlation addresses this issue because the drift between two consecutive images is unlikely to exceed the unit cell length.

Figure 7E:
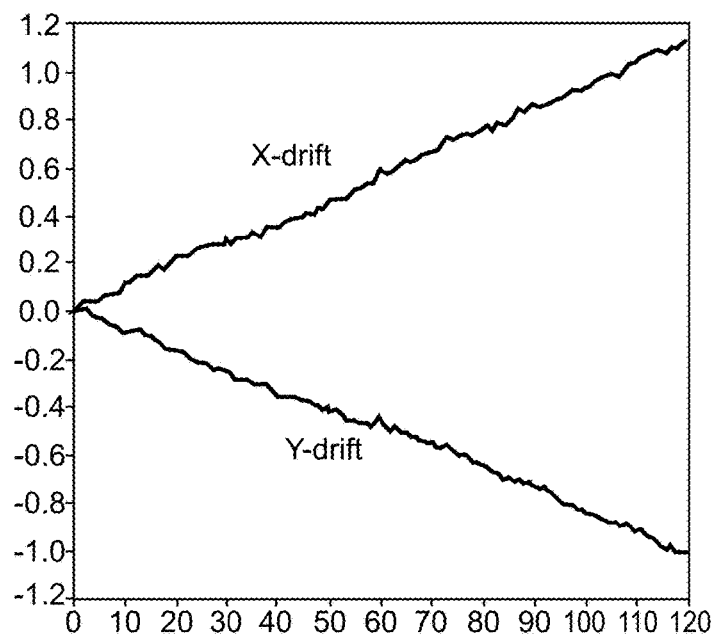
FIG. 7E illustrates a graph of drift plots across the X- and Y-axes for a sequence of images according to an embodiment.

FIG. 7E is a graph of an example of drift plots calculated from the cross-correlation, which shows the amount of drift in the X- and Y-axes for each image in the sequence relative to the previous image. Although these example drift plots are relatively linear, this may not occur in all implementations and the drift plots can take any form, depending upon the movement of the object during imaging, including one with appearing to contain random shifts.

The processor 116 then aligns the original images ($f_i$) in the sequence of images ($f_1(x,y)$, ($f_2(x,y)$, ..., ($f_n(x,y)$)) by applying the image shift information to each original image ($f_i$) in the sequence of images (step 625). Thus, a single iteration cycle of the cross-correlation includes a drift determination operation and a drift correction operation of all of the images in the sequence of images. Assuming that the drift correction determination includes m cycles and that the drift determined for image i (relative to image 1) at iterative cycle k is $r_{ik} = [\Delta x_{ik}, \Delta y_{ik}]$, the overall drift for image i, $r_i$ relative to image 1 is:

$$r_i = \sum_{k=1}^{m} [\Delta x_{ik}, \Delta y_{ik}] \qquad (8)$$

Thus, the overall alignment can be improved by performing a number of iterative cycles. In one embodiment, the number of iterative cycles is, for example, ten cycles.

Figure 7F:
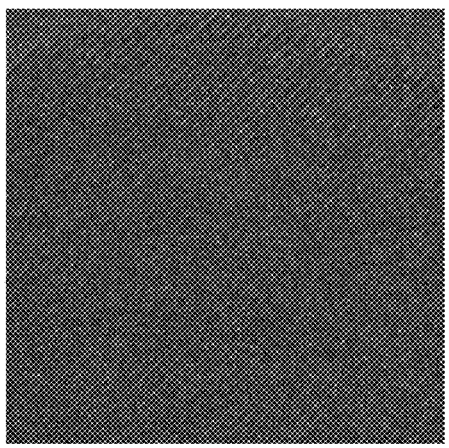
Figure 7G:
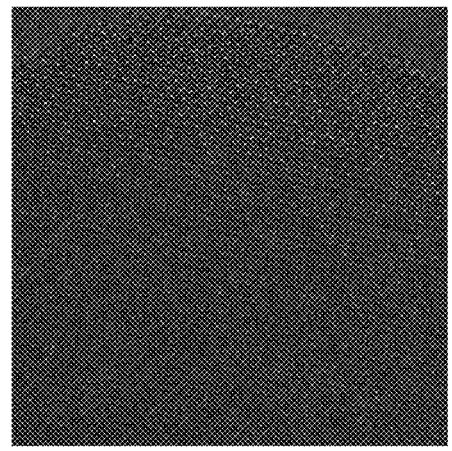

The processor 116 then sums the aligned images to form an image-shift-corrected summed image (step 630). The image-shift-corrected summed image can then be output, for example on a display via input/output interface 120 (step 635). FIG. 7F illustrates a summed image generated without performing any alignment of the images in the sequence of images and FIG. 7G illustrates summed images aligned in the manner described in connection with FIG. 6. As will be appreciated, the lattice features are much clearer in the summed images of FIG. 7G compared to that of FIG. 7F.

It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A method, comprising:
    applying an electron beam to a sample;
    obtaining an image of the sample with the applied electron beam;
    automatically determining an orientation of the sample relative to the sample's zone axis based on a distribution of reflections in the image; and
    automatically adjusting the orientation of the sample to align with the sample's zone axis based on the determined orientation.

2. The method of claim 1, wherein the automatic determination of the orientation of the sample further comprises:
    determining a Laue circle of the imaged sample based on the distribution of reflections in the image; and
    determining tilt angle adjustments based on the determined Laue circle.

3. The method of claim 2, wherein the determination of tilt angle adjustments further comprises:
    determining an angle between a path of the electron beam to the sample and a first line connecting a center of the Laue circle and a center of an Ewald sphere.

4. The method of claim 3, further comprising:
    decomposing the determined angle into a first axis component and a second axis component.

5. The method of claim 4, wherein the decomposition of the determined angle into the first and second axis components comprises:
    determining a first vector, which is perpendicular to a α-tilt axis, from the center of the Laue circle to a point on the first axis;
    determining the first axis component as an angle between the first line and a second line connecting the point on the first axis to the center of the Ewald Sphere; and determining the second axis component as an angle between the second line and a third line corresponding to the path of the electron beam to the sample.

6. The method of claim 4, wherein the decomposition of the determined angle into the first and second axis components comprises:
   determining a first vector, which is perpendicular to a α-tilt axis, from the center of the Laue circle to a point on the first axis;
   determining the first axis component as an angle between the first line and a second line connecting the point on the first axis to the center of the Ewald Sphere; and
   determining the second axis component as a difference between the determined angle and the first axis component.

7. The method of claim 1, wherein after the orientation is automatically adjusted, the method comprises:
   applying the electron beam to the sample; and
   obtaining another image of the sample with the applied electron beam.

8. The method of claim 1, further comprising:
   receiving an operator input requesting zone axis alignment of the sample, wherein the method is automatically performed in response to receipt of the operator input.

9. A system, comprising:
   an electron gun;
   a sample holder;
   an imaging detector;
   a positioning controller coupled to the sample holder and configured to adjust an orientation of a sample in the sample holder; and
   a processor communicatively coupled to the electron gun, the sample holder, the imaging detector, and the positioning controller,
   wherein the processor executes instructions to control the sample holder based on an automatically calculated Laue circle of the imaged sample.

10. The system of claim 9, wherein the processor executes instructions to control the electron gun, the sample holder, the imaging detector, and the positioning controller to
   apply an electron beam from the electron gun to the sample;
   obtain an image of the sample with the applied electron beam from the imaging detector;
   automatically determine an orientation of the sample relative to the sample's zone axis based on the image based on the automatically calculated Laue circle; and
   automatically adjust, via the sample holder, the orientation of the sample to align with the sample's zone axis based on the determined orientation.

11. The system of claim 9, wherein the processor is configured to control an orientation of the sample in the sample holder by:
   determining tilt angle adjustments based on the calculated Laue circle using a distribution of reflections in the image of the sample.

12. The system of claim 11, wherein the processor is configured to determine the tilt angle adjustments by:
   determining an angle between a path of an electron beam from the electron gun to the sample and a first line connecting a center of the Laue circle and a center of an Ewald sphere.

13. The system of claim 12, wherein the processor is configured to:
   decompose the determined angle into a first axis component and a second axis component.

14. The system of claim 13, wherein the processor is configured to decompose the determined angle into the first and second axis components by:
   determining a first vector, which is perpendicular to a α-tilt axis, from the center of the Laue circle to a point on the first axis;
   determining the first axis component as an angle between the first line and a second line connecting the point on the first axis to the center of the Ewald Sphere; and
   determining the second axis component as an angle between the second line and a third line corresponding to the path of the electron beam to the sample.

15. The system of claim 14, wherein the processor is configured to decompose the determined angle into the first and second axis components by:
   determining a first vector, which is perpendicular to a α-tilt axis, from the center of the Laue circle to a point on the first axis;
   determining the first axis component as an angle between the first line and a second line connecting the point on the first axis to the center of the Ewald Sphere; and
   determining the second axis component as a difference between the determined angle and the first axis component.

16. The system of claim 9, further comprising:
   an operator input device configured to receive an operator input requesting zone axis alignment of the sample, wherein the processor is configured to automatically apply the electron beam, obtain the image of the sample, determine the orientation of the sample, and adjust the orientation of the sample in response to receipt of the operator input.

17. A method, comprising:
   automatically determining an orientation of a sample relative to the sample's zone axis based on a distribution of reflections in an image of the sample;
   automatically adjusting the orientation of the sample to align with the sample's zone axis based on the determined orientation;
   calculating an amplitude filtered pattern in a Fourier domain based on amplitude components of a plurality of Fourier transformed images of a sequence of images;
   replacing an amplitude component of the plurality of Fourier transformed images with the amplitude pattern to form a plurality of filtered Fourier transformed images;
   determining image shift information based on the plurality of filtered Fourier transformed images; and
   applying the image shift information to images in the sequence of images to form a plurality of aligned images.

18. The method of claim 17, further comprising:
   performing an inverse Fourier transform on the plurality of filtered Fourier transformed images to form a corresponding plurality of reverse transformed, filtered images, wherein the shift information is determined using the plurality of reverse transformed, filtered images.

19. The method of claim 18, wherein the determination of the image shift information comprises:
   cross-correlating the plurality of reverse transformed, filtered images with a consecutive one of the plurality of reverse transformed, filtered images to generate the image shift information for the plurality of reverse transformed, filtered images.

20. The method of claim 17, further comprising:
   summing the plurality of aligned images to form an image-shift-corrected summed image.

* * * * *